United States Patent [19]

Kleiner et al.

[11] Patent Number: 6,013,706

[45] Date of Patent: Jan. 11, 2000

[54] PROCESS FOR THE PREPARATION OF HYROLYSIS-STABLE TRIVALENT PHOSPHORUS COMPOUNDS AND THEIR USE AS STABILIZERS FOR THERMOPLASTICS

[75] Inventors: Hans-Jerg Kleiner, Kronberg/Taunus; Dieter Regnat, Frankfurt am Main; Gerhard Pfahler, Augsburg, all of Germany

[73] Assignee: Clariant GmbH, Germany

[21] Appl. No.: 08/293,577

[22] Filed: Aug. 22, 1994

Related U.S. Application Data

[63] Continuation of application No. 08/071,174, Jun. 2, 1993, abandoned.

[30] Foreign Application Priority Data

Jun. 4, 1992 [DE] Germany ............................ 42 8 411
Nov. 28, 1992 [DE] Germany ............................ 42 40 043

[51] Int. Cl.[7] .............................. C08K 5/53; C08K 15/32; C07F 9/02
[52] U.S. Cl. ..................... 524/126; 252/400.24; 558/78
[58] Field of Search ....................... 252/400.24; 524/126; 558/78

[56] References Cited

U.S. PATENT DOCUMENTS

| | | | |
|---|---|---|---|
| 3,240,751 | 3/1966 | Cannon et al. .......................... | 523/427 |
| 3,809,676 | 5/1974 | Liberti et al. ............................ | 524/135 |
| 4,086,304 | 4/1978 | Hutton et al. ............................ | 558/71 |
| 4,402,858 | 9/1983 | Capolupo et al. .................. | 252/400 A |
| 4,443,572 | 4/1984 | Burns ........................................ | 558/71 |
| 4,496,495 | 1/1985 | Caspari et al. .......................... | 558/146 |
| 4,504,613 | 3/1985 | Abolins et al. .......................... | 524/126 |
| 5,162,406 | 11/1992 | Meyer et al. ............................ | 524/126 |
| 5,208,362 | 5/1993 | Glass . | |

FOREIGN PATENT DOCUMENTS

| | | |
|---|---|---|
| 0143464 | 6/1985 | European Pat. Off. . |
| 0 400 454 | 12/1990 | European Pat. Off. . |
| 0 516 006 | 12/1992 | European Pat. Off. . |

OTHER PUBLICATIONS

Chemical Abstract, vol. 55. No. 24,27, "Hydrolysis of trialkyl phosphites in the presence of inorganic bases".
Göghová, M., et al, *Chem. Papers* 43:421–432 (1989).

*Primary Examiner*—Kriellion Sanders
*Attorney, Agent, or Firm*—Connolly Bove Lodge & Hutz LLP

[57] ABSTRACT

The hydrolysis stability of trivalent organic phosphorus compounds of the formula I

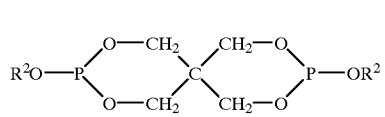

(II)

used as stabilizers for thermoplastics is improved if these compounds are treated with 0.01 to 5% by weight of an oxide, a carbonate, a hydroxide, a bicarbonate or a carboxylate of a metal of groups 1$a$, 2$a$, 2$b$ and 7$b$ of the periodic table of the elements. The storage stability and the ease of handling are increased and the discoloration of the stabilized polymers is reduced.

12 Claims, No Drawings

PROCESS FOR THE PREPARATION OF HYROLYSIS-STABLE TRIVALENT PHOSPHORUS COMPOUNDS AND THEIR USE AS STABILIZERS FOR THERMOPLASTICS

This application is a continuation of Ser. No. 08/071,174 filed Jun. 2, 1993, now abandoned.

Process for the preparation of hydrolysis-stable trivalent phosphorus compounds and their use as stabilizers for thermoplastics The invention relates to a process for the preparation of hydrolysis-stable trivalent organophosphorus compounds which are to be used as stabilizers for thermoplastics.

As is known, synthetic polymers must be protected from undesirable oxidative, thermal and photochemical damage during preparation, use and application by stabilizers or stabilizer systems. Such stabilizers comprise, for example, a phenolic antioxidant and one or more costabilizers, which sometimes also increase the action of the phenolic component synergistically. The customary costabilizers include, for example, ortho-alkylated aryl phosphites and phosphonites.

Such trivalent phosphorus compounds of industrial quality are not hydrolysis-stable in some cases and can then lose their stabilizing property in the course of time. They can also be split hydrolytically by atmospheric moisture, which means that storage stability decreases. Although the matter of hydrolysis stability is of great industrial importance, the reasons have not been very thoroughly investigated (cf. M. Göghova, Chem. Papers 43 (1989), 421–432). There are therefore also hardly any known measures which lead to an improvement in hydrolysis stability.

It is known that the hydrolysis stability of phosphites can be improved by addition of nitrogen-containing bases (cf. EP 143 464). The amount of amine added is 5 to 30% by weight. However, the addition of amines has various disadvantages, in particular an undesirable yellow coloration of the stabilized polymer.

There was therefore the object of discovering a process which improves the hydrolysis stability without the addition of such nitrogen-containing bases.

It has been found that treatment with certain inorganic compounds is capable of achieving the object.

The invention thus relates to a process for the preparation of hydrolysis-stable trivalent phosphorus compounds of the formula I $$P(OR^1)_3 \qquad (I)$$

of the formula II

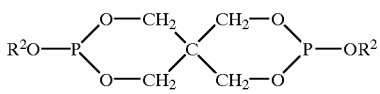

(II)

or of the formula III $$R^3\text{-}[P(OR^2)_2]_n \qquad (III)$$

wherein n is 1 or 2,

R$^1$ is a phenyl radical, which can be substituted by one or more linear or branched C$_1$–C$_8$-alkyl radicals or by C$_5$–C$_8$-cycloalkyl, C$_6$–C$_{10}$-aryl or C$_7$–C$_{10}$-aralkyl radicals, R$^2$ is a linear or branched C$_8$–C$_{20}$-alkyl radical or a phenyl radical, which can be substituted by one or more linear or branched C$_1$–C$_8$-alkyl radicals or by C$_5$–C$_8$-cycloalkyl, C$_6$–C$_{10}$-aryl or C$_7$–C$_{10}$-aralkyl radicals, R$^3$, if n=1, is a phenyl or benzyl radical, which can carry 1 to 3 substituents, an α-methylbenzyl, α,α-dimethylbenzyl or naphthyl radical or a naphthyl radical which carries 1 to 5 substituents, in which the substituents are identical or different and are a linear or branched C$_1$–C$_8$-alkyl radical, a C$_1$–C$_8$-alkoxy radical, a C$_1$–C$_{12}$-alkylthio radical, a C$_1$–C$_8$-dialkylamino radical, a C$_6$–C$_{10}$-aryl radical, a C$_6$–C$_{10}$-aryloxy radical or halogen having an atomic number of 9 to 35 and R$^3$, if n=2, is a phenylene radical, a biphenylene radical, a naphthylene radical or a diphenylene oxide radical, which are unsubstituted or carry 1 to 4 linear or branched C$_1$–C$_8$-alkyl radicals, which comprises treating the compounds of the formula I, II or III with 0.005 to 5% by weight of an oxide, a hydroxide, a carbonate, a bicarbonate or a carboxylate of a metal of groups 1a, 2a, 2b and 7b of the periodic table of the elements.

The invention furthermore relates to the use of these compounds as stabilizers for thermoplastics, and to the molding compositions containing these compounds.

Trivalent organic phosphorus compounds of industrial quality are treated by the process according to the invention. These phosphorus compounds are those of the formula I $$P(OR^1)_3 \qquad (I)$$

of the formula II

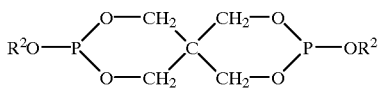

(II)

or of the formula III $$R^3\text{-}[P(OR^2)_2]_n \qquad (III)$$

In these formulae n is 1 or 2,

R$^1$ is a phenyl radical, which can be substituted by one or more linear or branched C$_1$–C$_8$-alkyl radicals or by C$_5$–C$_8$-cycloalkyl, C$_6$–C$_{10}$-aryl or C$_7$–C$_{10}$-aralkyl radicals, preferably 2,4-di-t-butylphenyl radicals, R$^2$ is a linear or branched C$_8$–C$_{20}$-alkyl radical, or is a phenyl radical, which can be substituted by one or more linear or branched C$_1$–C$_8$-alkyl radicals or by C$_5$–C$_8$-cycloalkyl, C$_6$–C$_{10}$-aryl or C$_7$–C$_{10}$-aralkyl radicals, preferably a C$_{18}$-alkyl radical or 2,4-di-t-butylphenyl radical, R$^3$, if n=1, is a phenyl or benzyl radical, which can carry 1 to 3 substituents, an α-methylbenzyl, α,α-dimethylbenzyl or naphthyl radical or a naphthyl radical which carries 1 to 5 substituents, in which the substituents are identical or different and are a linear or branched C$_1$–C$_8$-alkyl radical, a C$_1$–C$_8$-alkoxy radical, a C$_1$–C$_{12}$-alkylthio radical, a C$_1$–C$_8$-dialkylamino radical, a C$_6$–C$_{10}$-aryl radical, a C$_6$–C$_1$O-aryloxy radical or halogen having an atomic number of 9 to 35, and preferably a naphthyl or biphenyl radical, and R$^3$, if n=2, is a phenylene radical, a biphenylene radical, a naphthylene radical or a diphenylene oxide radical, which are unsubstituted or carry 1 to 4 linear or branched C$_1$–C$_8$-alkyl radicals, preferably a biphenylene or naphthylene radical.

Preferred compounds of the formula I are tris (nonylphenyl) phosphite and tris(2,4-di-t-butylphenyl) phosphite.

Preferred compounds of the formula II are pentaerythrityl spiro-bis-(2,4-di-t-butylphenyl) phosphite and pentaerythrityl spiro-bis(stearyl) phosphite.

Compounds of the formula III which are preferably employed are 1-naphthyl-phosphonous acid bis-(2,4-di-t-butylphenyl) phosphonite, tetrakis-(2,4-di-t-butyl-phenyl)-4,4'-biphenylene diphosphonite, 2,4,6-trimethyl-phenyl-phosphonous acid bis-(2,4-di-t-butylphenyl) phosphonite and tetrakis-(2,4-di-t-butylphenyl)-4,4'-diphenylene oxide diphosphite.

Tetrakis-(2,4-di-t-butylphenyl)-4,4'-biphenylene diphosphonite is particularly preferably employed. This compound can be obtained by the processes known to date only as a mixture with compounds which are position isomers to it, biphenyl monophosphonites which are position isomers and other trivalent phosphorus compounds, the product mixtures having a varying hydrolysis lability and being not easy to handle for industrial purposes.

The compounds of the formulae I, II and III are treated with an oxide, hydroxide, carbonate, bicarbonate or carboxylate, preferably a $C_1$–$C_8$-carboxylate, of a metal of groups 1a, 2a, 2b or 7b. Preferred metals are lithium, calcium, barium, magnesium, zinc and manganese, particularly preferably magnesium. Suitable oxides are magnesium oxide, calcium oxide, barium oxide and zinc oxide, suitable carbonates are lithium carbonate, magnesium carbonate, calcium carbonate and zinc carbonate, and suitable carboxylates are manganese acetate and zinc acetate. Magnesium oxide, zinc oxide, zinc carbonate and magnesium carbonate are preferred for treatment in solution or suspension, and magnesium oxide, lithium hydroxide, lithium carbonate and magnesium carbonate are preferred for treatment in the melt. The metal compound is employed in an amount of 0.005 to 5, preferably 0.05 to 2.0% by weight, based on the phosphorus compound.

The treatment of the phosphorus compound with the metal compound in solution or suspension is carried out by mixing the compounds either in the dry state or in a solvent or suspending agent. Possible solvents or suspending agents are, for example, tetrahydrofuran, methylcyclohexane, toluene, chlorobenzene, methanol, ethanol, isopropanol or water. If a solvent or suspending agent is used, the phosphorus compound and the metal compound are dissolved or suspended and the solution or suspension is stirred or digested for some time. In this case, the metal compound can be separated off.

A particularly preferred treatment method is suspension of the phosphorus compound and the metal compound in water, stirring, removal of the solid, taking up of the residue in a solvent and removal of the insoluble constituents. The solution is evaporated and the solid product is comminuted.

The treatment is carried out at a temperature from 10 to 100° C., preferably 15 to 50° C., and as a rule lasts 1 minute to 24 hours, preferably 2 minutes to 1 hour.

The treatment of the phosphorus compound with the metal compound in the melt is carried out by admixing the metal compounds with the molten phosphorus compound. When the treatment has been carried out, the melt is allowed to cool and the solid product is comminuted. It may be advantageous to dissolve the phosphorus compounds in a solvent after the treatment with the metal compound, to remove insoluble residues and then to isolate the product by distilling off the solvent. Possible suitable solvents are, for example, tetrahydrofuran, methylcyclohexane, toluene, chlorobenzene, dichlorobenzene or isopropanol.

The treatment is carried out at a temperature of 20 to 250° C., preferably 70 to 200° C., in particular 100 to 150° C., and as a rule lasts 1 minute to 24 hours, preferably 2 minutes to 5 hours.

The phosphorus compounds treated in this manner are distinguished by a particular hydrolysis stability and storage stability, even under extreme conditions.

The phosphorus compounds treated according to the invention are employed as stabilizers for thermoplastics, being combined with a phenolic antioxidant if appropriate.

The plastics molding composition according to the invention comprises a thermoplastic organic polymer, for example one of those listed below:

1. Polymers of mono- and diolefins, for example polyethylene of high, medium or low density (which can optionally be crosslinked), polypropylene, polyisobutylene, polybut-1-ene, polymethylpent-1-ene, polyisoprene or polybutadiene, and polymers of cycloolefins, such as, for example, of cyclopentene or norbornene.

2. Mixtures of the polymers mentioned under 1), for example mixtures of polypropylene with polyethylene or with polyisobutylene.

3. Copolymers of mono- and diolefins with one another or with other vinyl monomers, such as, for example, ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and salts thereof (ionomers), and terpolymers of ethylene with propylene and a diene, such as hexadiene, cyclopentadiene or ethylidenenorbornene.

4. Polystyrene and poly(p-methylstyrene).

5. Copolymers of styrene or α-methylstyrene with dienes or acrylic derivatives, such as, for example, styrene/butadiene, styrene/maleic anhydride, styrene/acrylonitrile, styrene/ethyl methacrylate, styrene/butadiene/ethyl acrylate and styrene/acrylonitrile/methacrylate; high impact strength mixtures of styrene copolymers and another polymer, such as, for example, a polyacrylate, a diene polymer or an ethylene/propylene/diene terpolymer; and block copolymers of styrene, such as, for example, styrene/butadiene/styrene, styrene/isoprene/styrene, styrene/ethylene-butylene/styrene or styrene/ethylenepropylene/styrene.

6. Graft copolymers of styrene, such as, for example, styrene on polybutadiene, styrene and acrylonitrile on polybutadiene, styrene and maleic anhydride on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under 5), which are known, for example, as so-called ABS, MBS, ASA or AES polymers.

7. Polyvinyl chloride.

8. Copolymers of vinyl chloride, which can be prepared by the known processes (for example suspension, bulk or emulsion polymerization).

9. Copolymers of vinyl chloride with up to 30% by weight of comonomers, such as, for example, vinyl acetate, vinylidene chloride, vinyl ethers, acrylonitrile, acrylic acid esters, maleic acid mono- or diesters or olefins, and graft polymers of vinyl chloride.
10. Halogen-containing polymers, such as, for example, polychloroprene, chlorinated rubber, chlorinated or chlorosulfonated polyethylene, epichlorohydrin homo- and copolymers and in particular polymers of halogen-containing vinyl compounds, such as, for example, polyvinylidene chloride, polyvinyl fluoride and polyvinylidene fluoride; and copolymers thereof, such as copolymers of vinyl chloride/vinylidene chloride, vinyl chloride/vinyl acetate or vinylidene chloride/vinyl acetate.
11. Polymers which are derived from α,β-unsaturated acids and derivatives thereof, such as polyacrylates and polymethacrylates, polyacrylamides and polyacrylonitriles.
12. Copolymers of the monomers mentioned under 11) with one another or with other unsaturated monomers, such as, for example, acrylonitrile/butadiene copolymers, acrylonitrile/alkyl acrylate copolymers, acrylonitrile/alkoxyacrylate copolymers, acrylonitrile/vinyl halide copolymers or acrylonitrile/alkyl methacrylate/butadiene copolymers.
13. Polymers which are derived from unsaturated alcohols and amines or their acyl derivatives or acetals, such as polyvinyl alcohol, polyvinyl acetate, stearate, benzoate or maleate, polyvinylbutyral, polyallyl phthalate and polyallylmelamine.
14. Homo- and copolymers of cyclic ethers, such as polyethylene glycols, polyethylene oxide, polypropylene oxide or copolymers thereof with bisglycidyl ethers.
15. Polyacetals, such as polyoxymethylene, and those polyoxymethylenes which contain comonomers, such as, for example, ethylene oxide.
16. Polyphenylene oxides and sulfides and mixtures thereof with styrene polymers.
17. Polyurethanes which are derived from polyethers, polyesters and polybutadienes having terminal hydroxyl groups on the one hand and aliphatic or aromatic polyisocyanates on the other hand, and precursors thereof (polyisocyanate-polyol prepolymers).
18. Polyamides and copolyamides which are derived from diamines and dicarboxylic acids and/or from aminocarboxylic acids or the corresponding lactams, such as polyamide 4, polyamide 6, polyamide 6,6, polyamide 6,10, polyamide 11, polyamide 12, poly-2,4,4-trimethylhexamethylene terephthalamide and poly-m-phenylene isophthalamide, and copolymers thereof with polyethers, such as, for example, with polyethylene glycol, polypropylene glycol or polytetramethylene glycol.
19. Polyureas, polyimides and polyamide-imides.
20. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-(2,2-bis-(4-hydroxyphenyl)propane) terephthalate and polyhydroxybenzoates, and block polyether-esters which are derived from polyethylene having hydroxyl end groups, dialcohols and dicarboxylic acids.
21. Polycarbonates and polyester-carbonates.
22. Polysulfones, polyether-sulfones and polyether-ketones.
23. Crosslinked polymers which are derived from aldehydes on the one hand and phenols, urea or melamine on the other hand, such as phenol/formaldehyde, urea/formaldehyde and melamine/formaldehyde resins.
24. Drying and non-drying alkyd resins.
25. Unsaturated polyester resins which are derived from copolyesters of saturated and unsaturated dicarboxylic acids with polyhydric alcohols, and vinyl compounds as crosslinking agents, and also halogen-containing, poorly combustible modifications thereof.
26. Crosslinkable acrylic resins which are derived from substituted acrylic acid esters, such as, for example, epoxyacrylates, urethane-acrylates or polyester-acrylates.
27. Alkyd resins, polyester resins and acrylate resins which are crosslinked with melamine resins, urea resins, polyisocyanates or epoxy resins.
28. Crosslinkable epoxy resins which are derived from polyepoxides, for example from bis-glycidyl ethers or from cycloaliphatic diepoxides.
29. Naturally occurring polymers, such as cellulose, natural rubber, gelatin and polymer-homologous, chemically modified derivatives thereof, such as cellulose acetates, propionates and butyrates, or cellulose ethers, such as methylcellulose.
30. Mixtures of the abovementioned polymers, such as, for example, PP/EPDM, polyamide 6/EPDM or ABST PVC/EVA, PVC/ABS, PVC/MBS, PC/ABS, PBTP/ABS, PC/ASA, PC/PBT, PVC/CPE, PVD/acrylate, POM/thermoplastic PUR, POM/acrylate, POM/MBS, PPE/HIPS, PPE/polyamide 6,6 and copolymers, PA/HDPE, PA/PP and PA/PPE.
30. Mixes of the abovementioned polymers, such as, for example, PP/EPDM, polyamide 6/EPDM or ABS, PVC/EVA, PVC/ABS, PVC/MBS, PC/ABS, PBTP/ABS, PC/ASA/ PC/PBT, PVC/CPE, PVD/acrylate, POM/thermoplastic PUR, POM/acrylate, POM/MBS, PPE/HIPS, PPE/polyamide 6,6 and copolymers, PA/HDPE, PA/PP and PA/PPE.
31. Naturally occurring and synthetic organic substances which are pure monomers or mixtures of monomers, such as, for example, mineral oils, animal and vegetable fats, oils and waxes or oils, fats and waxes based on synthetic esters, or mixtures of these substances.
32. Aqueous dispersions of natural or synthetic rubber.

The additives are incorporated into the organic polymers in accordance with the generally customary methods. The incorporation can be carried out, for example, by mixing the compounds, and if appropriate further additives, into or applying them to the polymer immediately after the polymerization or into the melt before or during shaping. The incorporation can also be carried out by application of the dissolved or dispersed compounds to the polymer directly or mixing into a solution, suspension or emulsion of the polymer, if appropriate subsequently allowing the solvent to evaporate. The compounds are also active if they are subsequently incorporated into an already granulated polymer in a separate processing step.

The compounds to be used according to the invention can also be added in the form of a masterbatch, which comprises these compounds, for example, in a concentration of 1 to 75, preferably 2.5 to 30% by weight, to the polymers to be stabilized.

The organic polymers to be stabilized can additionally also contain the following antioxidants, such as, for example:

1. Alkylated monophenols, for example 2,6-di-t-butyl-4-methylphenol, 2-t-butyl-4,6-dimethylphenol, 2,6-di-t-butyl-4-ethylphenol, 2,6-di-t-butyl-4-i-butylphenol, 2,6-di-cyclopentyl-4-methylphenol, 2-(α-methylcyclohexyl)-4,6-dimethylphenol, 2,6-di-octadecyl-4-methylphenol, 2,4,6-tri-cyclohexylphenol and 2,6-di-t-butyl-4-methoxymethylphenol.

2. Alkylated hydroquinones, for example 2,6-di-t-butyl-4-methyoxyphenol, 2,5-di-t-butyl-hydroquinone, 2,5-di-t-amyl-hydroquinone and 2,6-diphenyl-4-octadecyloxyphenol.

3. Hydroxylated thiodiphenyl ethers, for example 2,2'-thio-bis-(6-t-butyl-4-methylphenol), 2,2'-thio-bis-(4-octylphenol), 4,4'-thio-bis-(6-t-butyl-3-methylphenol) and 4,4'-thio-bis-(6-t-butyl-2-methylphenol).

4. Alkylidene-bisphenols, for example 2,2'-methylene-bis-(6-t-butyl-4-methylphenol), 2,2'-methylene-bis(6-t-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-t-butylphenol), 2,2'-ethylidene-bis-(4,6-di-t-butylphenol), 2,2'-ethylidene-bis-(6-t-butyl-4-isobutylphenol), 2,2'-methylene-bis-[6-(α-methylbenzyl)-4-nonylphenol], 2,2'-methylene-bis-[6-(α,α-dimethylbenzyl)-4-nonylphenol], 4,4'-methylene-bis-(2,6-di-t-butylphenol), 4,4'-methylene-bis-(6-t-butyl-2-methylphenol), 1,1-bis-(5-t-butyl-4-hydroxy-2-methylphenyl)-butane, 2,6-di-(3-t-butyl-5-methyl-2-hydroxybenzyl)-4-methylphenol, 1,1,3-tris-(5-t-butyl-4-hydroxy-2-methylphenyl)-butane, 1,1-bis-(5-t-butyl-4-hydroxy-2-methylphenyl)-3-n-dodecyl-mercaptobutane, di-(3-t-butyl-4-hydroxy-5-methylphenyl)-dicyclo-pentadiene, di-[2-(3'-t-butyl-2'-hydroxy-5'-methyl-benzyl)-6-t-butyl-4-methylphenyl] terephthalate and ethylene glycol bis-[3,3-bis-(3'-t-butyl-4'-hydroxyphenyl)-butyrate.

5. benzyl compounds, for example 1,3,5-tri-(3,5-di-t-butyl-4-hydroxybenzyl)-2,4,6-trimethylbenzene, di-(3,5-di-t-butyl-4-hydroxybenzyl) sulfide, isooctyl 3,5-di-t-butyl-4-hydroxybenzyl-mercaptoacetate, bis-(4-t-butyl-3-hydroxy-2,6-dimethylbenzyl)-dithiol terephthalate, 1,3,5-tris-(3,5-di-t-butyl-4-hydroxybenzyl) isocyanurate, 1,3,5-tris-(4-t-butyl-3-hydroxy-2,6-dimethylbenzyl) isocyanurate, 3,5-di-t-butyl-4-hydroxybenzyl-phosphonic acid dioctadecyl ester and the calcium salt of 3,5-di-t-butyl-4-hydroxybenzyl-phosphonic acid monoethyl ester.

6. Acylaminophenols, for example 4-hydroxy-lauric acid anilide, 4-hydroxy-stearic acid anilide, 2,4-bis-octylmercapto-6-(3,5-di-t-butyl-4-hydroxy-anilino)-s-triazine and octyl N-(3,5-di-t-butyl-4-hydroxyphenyl)-carbamate.

7. Esters of β-(3,5-di-t-butyl-4-hydroxyphenyl)-propionic acid with mono- or polyhydric alcohols, such as, for example, with methanol, diethylene glycol, octadecanol, triethylene glycol, 1,6-hexanediol, pentaerythritol, neopentylglycol, tris-hydroxyethyl isocyanurate, thiodiethylene glycol or di-hydroxyethyl-oxalic acid diamide.

8. Esters of p-(5-t-butyl-4-hydroxy-3-methylphenyl)-propionic acid with mono- or polyhydric alcohols, such as, for example, with methanol, diethylene glycol, octadecanol, triethylene glycol, 1, 6-hexanediol, pentaerythritol, neopentylglycol, tris-hydroxyethyl isocyanurate, thiodiethylene glycol or di-hydroxyethyl-oxalic acid diamide.

9. Amides of β-(3,5-di-t-butyl-4-hydroxyphenyl)-propionic acid, such as, for example, N,N'-di-(3,5-di-t-butyl-4-hydroxyphenylpropionyl)-hexamethylenediamine, N,N'-di-(3,5-di-t-butyl-4-hydroxyphenylpropionyl)-trimethylenediamine and N,N'-di-(3,5-di-t-butyl-4-hydroxyphenylpropionyl)-hydrazine.

In addition, the polymers to be stabilized can also contain other additives, such as, for example:

1. UV adsorbers and light stabilizers
    1.1 2-(2'-Hydroxyphenyl)-benzotriazoles, such as, for example, the 5'-methyl, 3',5'-di-t-butyl, 5'-t-butyl, 5'-(1,1,3,3-tetramethylbutyl), 5-chloro-3',5'-di-t-butyl, 5-chloro-3'-t-butyl-5'-methyl, 3'-sec-butyl-5'-t-butyl, 4'-octoxy, 3',5'-di-t-amyl and 3',5'-bis(α,α-dimethylbenzyl) derivatives.
    1.2 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.
    1.3 Esters of optionally substituted benzoic acids, for example 4-t-butyl-phenyl salicylate, phenyl salicylate, octylphenyl salicylate, dibenzoylresorcinol, bis-(4-t-butylbenzoyl) resorcinol, benzoylresorcinol, 2,4-di-t-butylphenyl 3,5-di-t-butyl-4-hydroxybenzoate and hexadecyl 3,5-di-t-butyl-4-hydroxybenzoate.
    1.4 Acrylates, for example ethyl and isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate and N-(β-carbomethoxy-9-cyano-vinyl)-2-methyl-indoline.
    1.5 Nickel compounds, for example nickel complexes of 2,2'-thio-bis-[4-(1,1,3,3-tetramethyl-butyl)-phenol], such as the 1:1 or 1:2 complex, if appropriate with additional ligands, such as n-butyl-amine, triethanolamine or N-cyclohexyl-diethanolamine, nickel alkyl-dithiocarbamates, nickel salts of 4-hydroxy-3,5-di-t-butyl-benzylphosphonic acid monoalkyl esters, such as of the methyl or ethyl ester, nickel complexes of ketoximes, such as of 2-hydroxy-4-methyl-phenyl undecyl ketoxime, nickel complexes of 1-phenyl-4-lauroyl-5-hydroxy-pyrazole, if appropriate with additional ligands, and nickel salts of 2-hydroxy-4-alkoxybenzophenones.
    1.6 Sterically hindered amines, for example
        1.6.1 Bis-(2,2,6,6-tetramethylpiperidyl) sebacate, bis-(1,2,2,6,6-pentamethylpiperidyl) sebacate, bis-(2,2,6,6-tetramethylpiperidyl) glutarate, bis-(1,2,2,6,6-pentamethylpiperidyl) glutarate, bis-(2,2,6,6-tetramethylpiperidyl) succinate, bis-(1,2,2,6,6-pentamethylpiperidyl)-succinate, 4-stearyloxy-2,2,6,6-tetramethylpiperidine, 4-stearyloxy-1,2,2,6,6-pentamethylpiperidine, 4-stearoyloxy-2,2,6,6-tetramethylpiperidine, 4-stearoyl-oxy-1,2,2,6,6-pentamethylpiperidine, 2,2,6,6-tetramethylpiperidyl behenate, 1,2,2,6,6-pentamethylpiperidyl behenate, 2,2,4,4-tetramethyl-7-oxa-3,20-diazadispiro-[5.1.11.2]-heneicosan-21-one, 2,2,3,4,4-penta-methyl-7-oxa-3,20-diazadispiro-[5.1.11.2]-heneicosan-21-one, 2,2,4,4-tetramethyl-3-acetyl-7-oxy-3,20-diaza-dispiro-[5.1.11.2]-heneicosan-21-one, 2,2,4,4-tetramethyl-7-oxa-3,20-diaza-20-(β-lauryl-oxycarbonylethyl)-21-oxo-dispiro-[5.1.11.2]-heneicosane, 2,2,3,4,4-pentamethyl-7-oxa-3,20- diaza-20-(β-lauryloxy-carbonylethyl)-21-oxo-dispiro-[5.1.11.2]-heneicosane, 2,2,4,4-tetramethyl-3-acetyl-7-oxa-3,20-diazo-20-(β-lauryloxycarbonyl-ethyl)-21-oxo-dispiro-[5.1.11.2]-heneicosane, 1,1',3,3',5,5'-hexahydro-2,2',4,4',6,6'-hexaaza-2,2',6,6'-bismethano-7,8-dioxo-4,4'-bis-(1,2,2,6,6-pentamethyl-4-piperidyl)biphenyl, N,N',N'',N'''-tetrakis-[2,4-bis-[N-(2,2,6,6-tetramethyl-4-piperidyl)-butylamino]-1,3,5-triazin-6-yl]-4,7-diazadecane-1,10-diamine, N,N',N'',N'''-tetrakis[2,4-bis-[N(1,2,2,6,6-pentamethyl-4-piperidyl)-butylamino]-1,3,5-triazin-6-yl]-4,7-diazadecane-1,10-diamine, N,N',N'',N'''-tetrakis[2,4-bis-[N(2,2,6,6-tetramethyl-4-piperidyl)-methoxypropylamino]-1,3,5-triazin-6-yl]-4,7-diazadecane-1,10-diamine, N,N',N'',N'''-tetrakis[2,4-bis-[N-(1,2,2,6,6-pentamethyl-4-piperidyl)-methoxypropylamino]-1,3,5-triazin-6-yl]-4,7-diazadecane-1,10-diamine, bis-(1,2,2,6,6,-pentamethyl-piperidyl)-n-butyl-3,5-di-t-butyl-4-hydroxy-benzyl malonate, tris-(2,2,6,6-tetramethyl-4-piperidyl) nitrilotriacetate, tetrakis-(2,2,6,6-tetramethyl-4-piperidyl)-1,2,3,4-butanetetracarboxylic acid and 1,1'-(1,2-ethanediyl)-bis-(3,3,5,5-tetramethyl-piperazinone).

1.6.2 Poly-N,N'-bis-(2,2,6,6-tetramethyl-4-piperidyl)-1,8-diazadecylene, condensation product of 1-(2-hydroxyethyl)-2,2,6,6-tetramethyl-4-hydroxy-piperidine and succinic acid, the condensation product of N,N'-bis-(2,2,6,6-tetramethyl-4-piperidyl)-hexamethylenediamine and 4-t-octylamino-2,6-dichloro-1,3,5-triazine and the condensation product of N,N'-bis-(2,2,6,6-tetramethyl-4-piperidyl)-hexamethylenediamine and 4-morpholino-2,6-dichloro-1,3,5-triazine.

1.7 Oxalic acid diamide, for example 4,4'-di-octyloxy-oxanilide, 2,2'-di-octyloxy-5,5'-di-t-butyl-oxanilide, 2,2'-didodecyloxy-5,5'-di-t-butyloxanilide, 2-ethoxy-2'-ethyl-oxanilide, N,N'-bis-(3-dimethylaminopropyl)-oxalamide, 2-ethoxy-5-t-butyl-2'-ethyloxanilide and a mixture thereof with 2-ethoxy-2'-ethyl-5,4-di-t-butyl-oxanilide, and mixtures of o- and p-methoxy- and of o- and p-ethoxy-disubstituted oxanilides.

2. Metal deactivators, for example N, N '-diphenyloxalic acid diamide, N-salicylyl-N'-salicyloyl-hydrazine, N,N'-bis-salicyloyl-hydrazine, N,N'-bis-(3,5-di-t-butyl-4-hydroxyphenylpropionyl)-hydrazine, 3-salicyloylamino-1,2,3-triazole and bis-benzylidene-oxalic acid dihydrazide.

3. Phosphites and phosphonites, for example triphenyl phosphite, diphenyl alkyl phosphites, phenyl dialkyl phosphites, trisnonyl-phenyl phosphite, trilauryl phosphite, trioctadecyl phosphite, distearyl pentaerythrityl diphosphite, tris-(2,4-di-t-butylphenyl)-phosphite, diisodecyl pentaerythrityl diphosphite, bis-(2,4-di-t-butylphenyl)-pentaerythrityl diphosphite, tristearyl sorbityl triphosphite, tetrakis-(2,4-di-t-butylphenyl)-4,4'-biphenylene diphosphonite, 3,9-bis-(2,4-di-t-butylphenoxy)-2,4,8,10-tetraoxa-3,9-diphosphaspiro-[5,5]-undecane, tris-(2-t-butyl-4-thio-(2'-methenyl-4'-hydroxy-5'-t-butyl)-phenyl-5-methenyl)-phenyl phosphite.

4. Peroxide-destroying compounds, for example esters of p-thio-dipropionic acid, such as, for example, the lauryl, stearyl, myristyl or tridecyl esters, mercaptobenzimidazole, the zinc salt of 2-mercaptobenzimidazole, zinc alkyl-dithiocarbamate, dioctadecyl sulfide, dioctadecyl disulfide and pentaerythritol tetrakis-(β-dodecylmercapto)-propionate.

5. Basic costabilizers, for example melamine, polyvinylpyrrolidone, dicyandiamide, triallyl cyanurate, urea derivatives, hydrazine derivatives, amines, polyamines, polyurethanes, alkali metal and alkaline earth metal salts of higher fatty acids or phenolates, for example Ca stearate, Zn stearate, Mg stearate, Na ricinoleate, K palmitate, antimony pyrocatecholate or tin pyrocatecholate, and hydroxides and oxides of alkaline earth metals or of aluminum, for example CaO, MgO and ZnO.1

6. Nucleating agents, for example 4-t-butylbenzoic acid, adipic acid, diphenylacetic acid and dibenzylidenesorbitol.

7. Fillers and reinforcing agents, for example calcium carbonate, silicates, glass fibers, asbestos, talc, kaolin, mica, barium sulfate, metal oxides and hydroxides, carbon black and graphite.

8. Other additives, for example plasticizers, lubricants, emulsifiers, pigments, optical brighteners, flameproofing agents, antistatics and flowing agents.

The various additional additives of the abovementioned groups 1 to 6 are added to the polymers to be stabilized in an amount of 0.01 to 10, preferably 0.01 to 5% by weight, based on the total weight of the molding composition. The amount of additives of groups 7 and 8 is 1 to 80, preferably 10 to 50% by weight, based on the total molding composition.

The organic polymers stabilized according to the invention can be used in various forms, for example as films, fibers, tapes or profiles, as coating compositions or as binders for paints, adhesives or putties.

The following examples are intended to illustrate the invention further.

Comparison Example A

Preparation of tetrakis-(2,4-di-t-butylphenyl)-4,4'-biphenylene diphosphonite 200 mmol (=62.4 g) of 4,4'-dibromobiphenyl were converted into the Grignard compound with 400 mmol (=14,6 g) of magnesium filings in 600 cm$^3$ of tetrahydrofuran under the action of ultrasound (40 kHz). A solution of 400 mmol (=190.8 g) of phosphorous acid bis-(2,4-di-t-butylphenyl ester) chloride in 400 cm$^3$ of tetrahydrofuran/n-heptane 1:2 was added dropwise to the resulting suspension at −20 to −10° C. The batch was stirred at 0° C. for a further hour and at room temperature for 2 hours. Thereafter, the magnesium salt was filtered off and washed with 250 cm$^3$ of tetrahydrofuran/n-heptane 1:4. After the filtrate had been concentrated in vacuo and the residue had been powdered, 220 g of pale yellow powder with a content of the abovementioned compound of 76% ($^{31}$P-NMR) were obtained.

EXAMPLE 1

In each case 3 mmol of metal oxide or carbonate were introduced into 100 cm$^3$ of water and 25 mmol (=25 g) of the phosphorus compound prepared according to Comparison Example A were added, while mixing intensively, the batch was stirred for 10 minutes, and the solid was filtered off and dried in vacuo. In each case 25 g of a pale yellow powder in which the content of tetrakis-(2,4-di-t-butylphenyl)-4,4'- biphenylene diphosphonite had remained unchanged by the treatment, according to $^{31}$P-NMR, were obtained. The improved hydrolysis stability of the products can be seen from Table 1.

The following metal compounds were employed:

1a) 125 mg of MgO
1b) 250 mg of MgCO$_3$
1c) 175 mg of CaO
1d) 200 mg of ZnO
1e) 480 mg of BaO

To measure the hydrolysis stability, in each case 5 g of the powder were suspended in 95 cm$^3$ of water with addition of 0.1 g of a nonionic emulsifier, the suspension was stirred at 40° C. for 6 hours and the pH of the liquid was then determined.

EXAMPLE 2

In each case 5 g of the yellowish powder obtained according to Example 1a to 1e were mixed with 50 cm$^3$ of methylcyclohexane, the insoluble constituents were filtered off and the solvent was distilled off in vacuo to give, after powdering of the residue 5 g of a pale yellow powder, the composition of which had remained unchanged by the treatment, according to $^{31}$P-MNR. The hydrolysis stability of the resulting products was determined as in Example 1 and is likewise listed in Table 1.

TABLE 1

| Example | pH |
|---|---|
| Comparison A | 3.0 |
| 1a | 9.0 |
| 1b | 8.8 |
| 1c | 6.8 |
| 1d | 6.5 |
| 1e | 5.4 |
| 2a | 7.5 |
| 2b | 9.0 |
| 2e | 6.2 |

EXAMPLE 3

Preparation of a hydrolysis-stable tetrakis-(2,4-di-t-butylphenyl)-4,4'-biphenylene diphosphonite (from the product according to DE 21 52 481; content of 41.9%)

250 mg of magnesium oxide were mixed with 50 g of tetrakis-(2,4-di-t-butylphenyl)-4,4'-biphenylene diphosphonite in a mixer/homogenizer for 15 minutes, and the powder thus obtained was dissolved in 250 cm$^3$ of toluene. The solution was stirred for 24 hours, a filter aid (®Corolite 2) was added and the mixture was filtered. The filtrate was freed from the toluene in vacuo (final bath temperature of 35° C.). 47 g of a pale yellow powder with a content of the abovementioned compound of 41.4% ($^{31}$P-NMR) were obtained.

To measure the hydrolysis stability, in each case 5 g of the powder were suspended in 95 cm$^3$ of water with the addition of 0.1 g of a nonionic emulsifier, the mixture was stirred at 40° C. for 4 hours and the pH of the liquid was then determined.

| | |
|---|---|
| Untreated: | 3.24 |
| Treated: | 7.85 |

To measure the heat stability, the powder thus prepared and untreated tetrakis-(2,4-di-t-butylphenyl)-4,4'-biphenylene diphosphonite were heated at 120° C. in air for 6 hours and the content of diphosphonite was then determined by means of $^{31}$P-NMR.

| | |
|---|---|
| Untreated: | 20.6% |
| Treated: | 36.2%. |

EXAMPLE 4

Preparation of a hydrolysis-stable di-(2,4-di-t-butylphenyl)-pentaerythritol diphosphite (from the product according to EP 143 464)

450 mg of magnesium oxide were introduced into 350 cm$^3$ of water, and 90 g of di-(2,4-di-t-butylphenyl)-pentaerythritol diphosphite were added, while mixing intensively, the suspension was stirred for 40 minutes, and the solid substance was filtered off and dried. The product was dissolved in 350 cm$^3$ of toluene, and the solution was stirred with basic aluminum oxide, to remove residual amounts of water, and then filtered as in Example 3, using a filter aid. The filtrate was freed from the toluene in vacuo (final bath temperature of 40° C.). 85 g of di-(2,4-di-t-butylphenyl)-pentaerythritol diphosphite were obtained.

To measure the hydrolysis stability, in each case 5 g of the powder were suspended in 95 cm$^3$ of water with the addition of 0.1 g of a nonionic emulsifier, the suspension was stirred at 40° C. for 1 hour and the pH of the liquid was then determined.

| | |
|---|---|
| Untreated: | 1.95 |
| Treated: | 5.76 |

EXAMPLE 5

Preparation of a hydrolysis-stable tetrakis-(2,4-di-t-butylphenyl)-4,4'-biphenylene diphosphonite 50 g of tetrakis-(2,4-di-t-butylphenyl)-4,4'-biphenylene diphosphonite (prepared according to DE 21 52 481; content of 41.9%) were heated to 130° C. under a nitrogen atmosphere. 82 mg of magnesium oxide were added to the melt, while stirring, and the mixture was heated briefly to 150° C. The melt was then kept at 130° C. for 1 hour, while stirring, and subsequently cooled. The product was powdered. To measure the hydrolysis stability, 5 g of the powder were suspended in 95 cm$^3$ of water with the addition of 0.1 g of a nonionic emulsifier, the suspension was stirred at 90° C. for 4 hours and the pH of the liquid was then determined.

| | |
|---|---|
| Untreated pH | 3.31 |
| Treated pH | 7.98 |

EXAMPLE 6

100 g of tetrakis-(2,4-di-t-butylphenyl)-4,4'-biphenylene diphosphonite (product according to DE 21 52 481; content of 39%) were heated to 130° C under a nitrogen atmosphere. 123 mg of magnesium oxide were added to the melt, while stirring, and the mixture was kept at 130° C. for 1 hour, while stirring, and then cooled. The product was powdered.

The hydrolysis stability was determined as in Example 5.

| Untreated pH | 3.29 |
|---|---|
| Treated pH | 6.99 |

EXAMPLE 7

50 g of tetrakis-(2,4-di-t-butylphenyl)-4,4'-biphenylene diphosphonite (product according to DE 21 52 481; content of 39%) were heated to 130° C. under a nitrogen atmosphere. 82 mg of magnesium oxide were added to the melt, while stirring, and the mixture was heated briefly to 150° C. After 10 minutes, the batch was cooled. The product was powdered.

The hydrolysis stability was determined as in Example 5.

| Untreated pH | 3.30 |
|---|---|
| Treated pH | 8.13 |

To measure the heat stability, the powder thus treated and untreated starting substance were heated at 120° C in air for 24 hours and the content of diphosphonite was then determined by means of $^{31}$P-NMR.

| Untreated | 11.1% |
|---|---|
| Treated | 24.4% |

EXAMPLE 8

50 g of tetrakis-(2,4-di-t-butylphenyl)-4,4'-biphenylene diphosphonite (product according to DE 21 52 481; content of 39%) were heated to 130° C. under a nitrogen atmosphere. 76 g of lithium carbonate were added to the melt, while stirring, and the mixture was kept at 125 to 130° C. for 1 hour, while stirring, and then cooled. The product was powdered.

The hydrolysis stability was determined as in Example 5.

| Untreated pH | 3.28 |
|---|---|
| Treated pH | 6.06 |

The following products were employed for the Use Examples:

Product I: tetrakis-(2,4-di-t-butylphenyl)-4,4'-biphenylene diphosphonite, commercial product, Product II: tetrakis-(2,4-di-t-butylphenyl)-4,4'-biphenylene phosphonite, after-treated according to the invention in the absence of water (Example 3), Product III: tetrakis-(2,4-di-t-butylphenyl)-4,4'-biphenylene diphosphonite, after-treated according to the invention in the presence of water (Example 2a), Product IV: di-(2,4-di-t-butylphenyl)-pentaerythritol diphosphite, commercial product, Product V: di-(2,4-di-t-butylphenyl)-pentaerythritol diphosphite, after-treated according to the invention (Example 4).

EXAMPLE 9

To determine the storage stability, saturated KCl solution was introduced into a desiccator and kept at 60° C. After 2 days, a relative atmospheric humidity of 80° C had been established over the KCl solution. The test substances were then stored under these conditions (60° C., 80% relative atmospheric humidity). After 0, 4, 8, 24, 48, 72 and 144 hours, samples were removed, the decrease in active substance was determined by means of $^{31}$P-NMR spectroscopy and the times after which only half the amount of the original substances were detectable were recorded:

Product I (comparison): 20 hours

Product II: 138 hours

Product III: 64 hours

EXAMPLE 10

100.0 parts by weight of non-stabilized polypropylene powder (density: 0.903 g/cm$^3$; melt flow index MFI 230/5: 4 g/10 minutes) were mixed with 0.1 part by weight of Ca stearate as an acid acceptor, 0.05 part by weight of ethylene glycol bis-(3,3-bis-(3'-t-butyl-4'-hydroxyphenyl)-butyrate and the amounts of phosphorus compound stated in the tables, and the mixture was extruded several times by means of a laboratory extruder (short compression screw, screw diameter: 200 mm; length 20 D, die 30 mm long, 2 mm diameter; speed: 125 revolutions per minute; temperature program: 200/230/230° C.). After the 1st, 5th and 10th pass, samples were taken from the granules and the melt flow index according to DIN 53 735 and the yellowing, as the Yellowness Index according to ASTM D 1925-70, were measured on these samples.

The results are listed in Tables 2 and 3.

The phosphorus compound treated according to the invention keeps the melt viscosity of the molding composition at the highest level (lowest MFI value) with the highest constancy. It moreover leads to the best starting colors of the test specimens and to the smallest change in color after 10 granulations.

TABLE 2

Effect of phosphorus compounds on the processing stability of polypropylene. Melt flow index MFI 230/5 after several granulations (MFI in g/10 minutes).

| | MFI after | | |
|---|---|---|---|
| Phosphorus compound | 1st | 5th | 10th granulation |
| None | 7.5 | 12.5 | 18 |
| 0.05 part by weight of product IV (comparison) | 4 | 5 | 5.5 |
| 0.05 part by weight of product V | 4 | 5 | 5.5 |
| 0.05 part by weight of product I (comparison) | 4 | 5 | 8.5 |
| 0.05 part by weight of product II | 4 | 5 | 8.5 |
| 0.05 part by weight of product III | 4.5 | 5 | 8.5 |

TABLE 3

Color course (Yellowness Index according to ASTM D 1925–70) during several granulations of polypropylene.

| | YI after | | |
|---|---|---|---|
| Phosphorus compound | 1st | 5th | 10th granulation |
| None | 13 | 20 | 24 |
| 0.05 part by weight of product IV (comparison) | 6 | 15 | 22 |

TABLE 3-continued

Color course (Yellowness Index according to ASTM D 1925–70) during several granulations of polypropylene.

| Phosphorus compound | YI after | | |
|---|---|---|---|
| | 1st | 5th | 10th granulation |
| 0.05 part by weight of product V | 6 | 12 | 19 |
| 0.05 part by weight of product I (comparison) | 5 | 15 | 28 |
| 0.05 part by weight of product II | 5 | 12 | 27 |
| 0.05 part by weight of product III | 5 | 12 | 27 |

EXAMPLE 11

To determine the processing stability, 100.0 parts by weight of non-stabilized polypropylene powder (density: 0.903 g/cm$^3$; melt flow index MFI 230/5: 4 g/10 minutes) were mixed with 0.1 part by weight of Ca stearate as an acid acceptor, 0.05 part by weight of ethylene glycol bis-(3,3-bis-(3'-t-butyl-4'-hydroxy-phenyl)-butyrate and the amounts of phosphorus compound stated in the tables, and the mixture was kneaded at 200° C. by means of a laboratory kneader. The course of the torque with respect to time was recorded. The values are listed in Table 4.

TABLE 4

| Phosphorus compound | Kneading time/torque Nm | | | | | |
|---|---|---|---|---|---|---|
| | 10 | 20 | 30 | 40 | 50 | 60 |
| None | 11 | 8.5 | 7 | 4 | 2 | 1 |
| Product I (comparison) | 11 | 10 | 9 | 7 | 4 | 2 |
| Product II | 11 | 10.5 | 9 | 6.5 | 3 | 1 |
| Product III | 11 | 10.5 | 10 | 9 | 7 | 4 |

We claim:
1. A process for the preparation of hydrolysis-stable trivalent phosphorous compounds of the formula I

   (I)

of the formula II

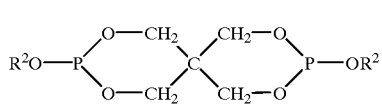   (II)

or the formula III

   (III)

wherein
n is 1 or 2
R$^1$ is a phenyl radical, which can be substituted by one or more linear or branched C$_1$–C$_8$-alkyl radicals or by C$_5$–C$_8$-cycloalkyl, C$_6$–C$_{10}$-aryl or C$_7$–C$_{10}$-aralkyl radicals,
R$^2$ is a linear or branched C$_8$–C$_{20}$-alkyl radical or a phenyl radical, which can be substituted by one or more linear or branched C$_1$–C$_8$-alkyl radicals or by C$_5$–C$_8$-cycloalkyl, C$_6$–C$_{10}$-aryl or C$_7$–C$_{10}$ aralkyl radicals, R$^3$, if n=1, is a phenyl or benzyl radical, which can carry 1 to 3 substituents, an α-methylbenzyl, α,α-dimethylbenzyl, or naphthyl radical or a naphthyl radical which carries 1 to 5 substituents, in which the substituents are identical or different and are a linear or branched C$_1$–C$_8$-alkyl radical, a C$_1$–C$_8$-alkoxy radical, a C$_1$–C$_{12}$-alkylthio radical, a C$_1$–C$_8$-dialkylamino radical, a C$_{6-C10}$-aryloxy radical or halogen having an atomic number of 9 to 35 and
R$^3$, if n=2, is a phenylene radical, a biphenylene radical, a naphthylene radical or a diphenylene oxide radical, which are unsubstituted or carry 1 to 4 linear or branched C$_1$–C$_8$-alkyl radicals,
which comprises the steps of:
treating the compounds of the formula I, II, or III in a solvent or a suspending agent with 0.005 to 5% by weight of an oxide, a hydroxide, a carbonate, a bicarbonate, or a carboxylate of a metal of groups 1a, 2a, 2d, or 7b of the periodic table of the elements, stirring the solution or suspension, and
isolating the phosphorous compound.
2. The process as claimed in claim 1, wherein the treatment is carried out in a suspending agent.
3. The process as claimed in claim 1, wherein the treatment is carried out in a solvent.
4. The process as claimed in claim 1, wherein the treatment is carried out in water.
5. The process as claimed in claim 1, wherein the treatment is carried out in a melt.
6. A method for stabilizing a thermoplastic comprising the step of:
providing a thermoplastic, and
stabilizing said thermoplastic with by incorporating the compound of claim 1 into said thermoplastic in an amount effective to provide stabilization.
7. The process as claimed in claim 1, wherein said hydrolysis-stable trivalent compound are compounds of formula I.
8. The process as claimed in claim 1, wherein said hydrolysis-stable trivalent phosphorous compounds are compounds of formula III.
9. A process for stabilizing thermoplastics, which comprises the steps of:
providing a thermoplastic material,
adding to the thermoplastic material 0.01 to 10% by weight of a phosphorous compound of the formula (I)

   (I)

of the formula II

   (II)

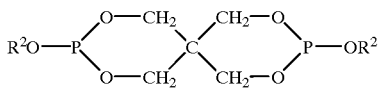

or of the formula III

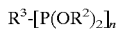   (III)

wherein
n is 1 or2
R$^1$ is a phenyl radical, which can be substituted by one or more linear or branched C$_1$–C$_8$-alkyl radicals or by C$_5$–C$_8$-cycloalkyl, C$_6$–C$_{10}$-aryl or C$_7$–C$_{10}$-aralkyl radicals, $R^2$ is a linear or branched $C_8$–$C_{20}$-alkyl radical or a phenyl radical, which can be substituted by one or more linear or branched $C_1$–$C_8$-alkyl radicals or by $C_5$–$C_8$-cycloalkyl, $C_6$–$C_{10}$-aryl or $C_7$–$C_{10}$ aralkyl radicals, $R^3$, if n=1, is a phenyl or benzyl radical, which can carry 1 to 3 substituents, an α-methylbenzyl, α,α-dimethylbenzyl, or naphthyl radical or a naphthyl radical which carries 1 to 5 substituents, in which the substituents are identical or different and are a linear or branched $C_1$–$C_8$-alkyl radical, a $C_1$–$C_8$-alkoxy radical, a $C_1$–$C_{12}$-alkylthio radical, a $C_1$–$C_8$-dialkylamino radical, a $C_6$–$C_{10}$-aryloxy radical or halogen having an atomic number of 9 to 35 and $R^3$, if n=2, is a phenylene radical, a biphenylene radical, a naphthylene radical or a diphenylene oxide radical, which are unsubstituted or carry 1 to 4 linear or branched $C_1$–$C_8$-alkyl radicals, which compound has been treated with 0.005 to 5% by weight of an oxide, a hydroxide, a carbonate, a bicarbonate, or a carboxylate of a metal of groups 1a, 2a, 2b, or 7b of the periodic table of the elements before addition of the compound to the polymer.

10. A thermoplastic molding composition comprising:
90 to 99.9% by weight of a thermoplastic polymer, and
0.01 to 10% by weight of a phosphorous compound of formula (I):

$$P(OR^1)_3 \tag{I}$$

of the formula II

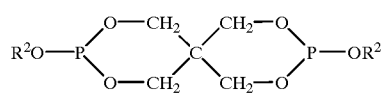
$$\tag{II}$$

or of the formula III

$$R^3\text{-}[P(OR^2)_2]_n \tag{III}$$

wherein n is 1 or 2

$R^1$ is a phenyl radical, which can be substituted by one or more linear or branched $C_1$–$C_8$-alkyl radicals or by $C_5$–$C_8$-cycloalkyl, $C_6$–$C_{10}$-aryl or $C_7$–$C_{10}$-aralkyl radicals, $R^2$ is a linear or branched $C_8$–$C_{20}$-alkyl radical or a phenyl radical, which can be substituted by one or more linear or branched $C_1$–$C_8$-alkyl radicals or by $C_5$–$C_8$-cycloalkyl, $C_6$–$C_{10}$-aryl or $C_7$–$C_{10}$ aralkyl radicals, $R^3$, if n=1, is a phenyl or benzyl radical, which can carry 1 to 3 substituents, an α-methylbenzyl, α,α-dimethylbenzyl, or naphthyl radical or a naphthyl radical which carries 1 to 5 substituents, in which the substituents are identical or different and are a linear or branched $C_1$–$C_8$-alkyl radical, a $C_1$–$C_8$-alkoxy radical, a $C_1$–$C_{12}$-alkylthio radical, a $C_1$–$C_8$-dialkylamino radical, a $C_6$–$C_{10}$-aryloxy radical or halogen having an atomic number of 9 to 35 and $R^3$, if n=2, is a phenylene radical, a biphenylene radical, a naphthylene radical or a diphenylene oxide radical, which are unsubstituted or carry 1 to 4 linear or branched $C_1$–$C_8$-alkyl radicals, wherein the compounds of the formulae I, II, or III have been treated with 0.005 to 5% by weight of an oxide, a hydroxide, a carbonate, a bicarbonate, or a carboxylate of a petal of groups 1a, 2a, 2b, or 7b of the periodic table of the elements.

11. A process for the preparation of hydrolysis-stable trivalent phosphorous compounds of the formula (I)

$$P(OR^1)_3 \tag{I}$$

of the formula II

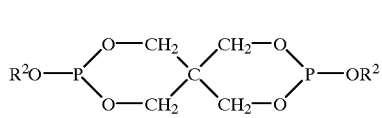
$$\tag{II}$$

or of the formula III

$$R^3\text{-}[P(OR^2)_2]_n \tag{III}$$

wherein n is1 or 2

$R^1$ is a phenyl radical, which can be substituted by one or more linear or branched $C_1$–$C_8$-alkyl radicals or by $C_5$–$C_8$-cycloalkyl, $C_6$–$C_{10}$-aryl or $C_7$–$C_{10}$-aralkyl radicals, $R^2$ is a linear or branched $C_8$–$C_{20}$-alkyl radical or a phenyl radical, which can be substituted by one or more linear or branched $C_1$–$C_8$-alkyl radicals or by $C_5$–$C_8$-cycloalkyl, $C_6$–$C_{10}$-aryl or $C_7$–$C_{10}$ aralkyl radicals, $R^3$, if n=1, is a phenyl or benzyl radical, which can carry 1 to 3 substituents, an α-methylbenzyl, α,α-dimethylbenzyl, or naphthyl radical or a naphthyl radical which carries 1 to 5 substituents, in which the substituents are identical or different and are a linear or branched $C_1$–$C_8$-alkyl radical, a $C_1$–$C_8$-alkoxy radical, a $C_1$–$C_{12}$-alkylthio radical, a $C_1$–$C_8$-dialkylamino radical, a $C_6$–$C_{10}$-aryloxy radical or halogen having an atomic number of 9 to 35 and $R^3$, if n=2, is a phenylene radical, a biphenylene radical, a naphthylene radical or a diphenylene oxide radical, which are unsubstituted or carry 1 to 4 linear or branched $C_1$–$C_8$-alkyl radicals, which comprises the steps of:
admixing 0.005 to 5% by weight of an oxide, a hydroxide, a carbonate, a bicarbonate, or a carboxylate of a metal of groups 1a, 2a, 2b or 7b of the periodic table of the elements with a molten phosphorous compound of formula I, II, or III, then
cooling the melt to form a solid product, then
comminuting the solid product, then
dissolving said comminuted solid product in a solvent whereby insoluble residues are removed, and
isolating the product by distilling off the solvent.

12. A process for the preparation of hydrolysis-stable trivalent phosphorous compounds of the formula (I)

$$P(OR^1)_3 \tag{I}$$

of the formula II

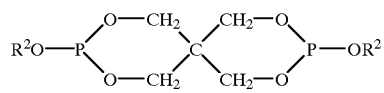 (II)

or the formula III

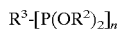 (III)

wherein n is 1 or 2

R$^1$ is a phenyl radical, which can be substituted by one or more linear or branched C$_1$–C$_8$-alkyl radicals or by C$_5$–C$_8$-cycloalkyl, C$_6$–C$_{10}$-aryl or C$_7$–C$_{10}$-aralkyl radicals, R$^2$ is a linear or branched C$_8$–C$_{20}$-alkyl radical or a phenyl radical, which can be substituted by one or more linear or branched C$_1$–C$_8$-alkyl radicals or by C$_5$–C$_8$-cycloalkyl, C$_6$–C$_{10}$-aryl or C$_7$–C$_{10}$ aralkyl radicals, R$^3$, if n=1, is a phenyl or benzyl radical, which can carry 1 to 3 substituents, an α-methylbenzyl, α,α-dimethylbenzyl, or naphthyl radical or a naphthyl radical which carries 1 to 5 substituents, in which the substituents are identical or different and are a linear or branched C$_1$–C$_8$-alkyl radical, a C$_1$–C$_8$-alkoxy radical, a C$_1$-C$_{,2}$-alkylthio radical, a C$_1$–C$_8$-dialkylamino radical, a C$_6$–C$_{10}$-aryloxy radical or halogen having an atomic number of 9 to 35 and R$^3$, if n=2, is a phenylene radical, a biphenylene radical, a naphthylene radical or a diphenylene oxide radical, which are unsubstituted or carry 1 to 4 linear or branched C$_1$–C$_8$-alkyl radicals, which consists essentially of the steps of:

admixing 0.005 to 5% by weight of an oxide, a hydroxide, a carbonate, a bicarbonate, or a carboxylate of a metal of groups 1a, 2a, 2b or 7b of the periodic table of the elements with a molten phosphorous compound of formula I, II, or III, then cooling the melt to form a solid product, then comminuting the solid product, then dissolving said comminuted solid product in a solvent whereby insoluble residues are removed, and isolating the product by distilling off the solvent.

* * * * *